US007417150B2

(12) United States Patent
Jeschke et al.

(10) Patent No.: US 7,417,150 B2
(45) Date of Patent: Aug. 26, 2008

(54) AZOLES HAVING AN INSECTICIDAL ACTION

(75) Inventors: Peter Jeschke, Bergisch Gladbach (DE); Michael Beck, Jüchen (DE); Wolfgang Krämer, Burscheid (DE); Detlef Wollweber, Wuppertal (DE); Christoph Erdelen, deceased, late of Leichlingen (DE); by Angelika Lubos-Erdelen, legal representative, Leichlingen (DE); Andreas Turberg, Haan (DE); Olaf Hansen, Leichlingen (DE); Hans-Dieter Martin, Düsseldorf (DE); Piet Sauer, Mettmann (DE)

(73) Assignee: Bayer CropScience AG, Monheim (DE)

( * ) Notice: Subject to any disclaimer, the term of this patent is extended or adjusted under 35 U.S.C. 154(b) by 690 days.

(21) Appl. No.: 10/474,947

(22) PCT Filed: Apr. 10, 2002

(86) PCT No.: PCT/EP02/03976

§ 371 (c)(1),
(2), (4) Date: Jul. 26, 2004

(87) PCT Pub. No.: WO02/085870

PCT Pub. Date: Oct. 31, 2002

(65) Prior Publication Data

US 2005/0009839 A1    Jan. 13, 2005

(30) Foreign Application Priority Data

Apr. 20, 2001  (DE) ............................... 101 19 423

(51) Int. Cl.
| | |
|---|---|
| *C07D 409/02* | (2006.01) |
| *C07D 277/50* | (2006.01) |
| *C07D 417/02* | (2006.01) |
| *A01N 43/10* | (2006.01) |
| *A01N 43/78* | (2006.01) |
| *C07D 411/00* | (2006.01) |
| *C07D 277/10* | (2006.01) |
| *A01K 31/44* | (2006.01) |
| *A01K 31/425* | (2006.01) |

(52) U.S. Cl. .................... 546/280.4; 548/190; 514/342; 514/370; 504/252; 504/266

(58) Field of Classification Search ............... 546/280.4; 548/190; 514/342, 370; 504/252, 266
See application file for complete search history.

(56) References Cited

U.S. PATENT DOCUMENTS

| | | | | |
|---|---|---|---|---|
| 4,098,791 A | 7/1978 | Hylton et al. | .......... | 260/293.87 |
| 4,284,642 A | 8/1981 | Toldy et al. | .............. | 424/273 R |
| 4,369,325 A | 1/1983 | Toldy et al. | ................. | 548/315 |
| 5,175,301 A | 12/1992 | Minamida et al. | ........... | 546/272 |
| 5,214,152 A | 5/1993 | Minamida et al. | ........... | 548/181 |
| 5,849,768 A | 12/1998 | Minamida et al. | ........... | 514/357 |
| 5,935,981 A | 8/1999 | Minamida et al. | ........... | 514/365 |
| 6,124,297 A | 9/2000 | Minamida et al. | ........... | 514/255 |
| 6,407,248 B1 | 6/2002 | Minamida et al. | ........... | 546/331 |

FOREIGN PATENT DOCUMENTS

| | | |
|---|---|---|
| CA | 1 264 472 | 1/1990 |
| CA | 1 267 905 | 4/1990 |
| DE | 2 921 683 | 12/1980 |
| DE | 29 21 683 | 12/1980 |
| EP | 0 192 060 | 8/1986 |
| EP | 0 483 055 | 4/1992 |
| EP | 0 547 557 | 6/1993 |
| EP | 0 697 410 | 2/1996 |
| JP | 46-26483 | 7/1971 |
| SU | 1392872 | 4/1998 |
| WO | 94/29268 | 12/1994 |

OTHER PUBLICATIONS

J. Heterocyclic Chem., 25, Nov.-Dec. 1988, pp. 1849-1856, Salma M. Abdelaal and Ludwig Bauer, "Synthesis of 2-Amino-4-imino-4,5-dihydrothiazoles from N-Sulfonyl-α-chloro-amidines and Thiourea [1]".

J. Chem. Soc. Perkin Trans. 1, (month unavailable) 1991, pp. 1201-1204, Stephen R. Landor et al, "5-Amino-3-imino-2,3-dihydrofurans and 3-Amino-5-imino-2,5-dihydrofurans from 4, 4-Dialkyl-4-hydroxybut-2-ynenitriles".

Translation from Zhurnal Organicheskoi Khimii, vol. 27, No. 3 pp. 526-530, Mar. 1991, "Cyanoacetylene and its Derivatives", Yu. M. Skvortsov et al, (see pp. 455-568 attached).

Translated from Zhurnal Organicheskoi Khimii, vol. 22, No. 2, pp. 255-259, Feb. 1986, Yu. M. Skvortsov et al, "Cyanoacetylene and Its Derivatives" (see pp. 222-226 attached).

Helvetica Chimica Acta, vol. 70 (month unavailable) 1987, pp. 1001-1011, Peter Wipf, Christjohannes Jenny und Heinz Heimgartner, "2,4-Bis(4-methylphenylthio)-1,3,2$\lambda^5$,4$\lambda^5$-dithiadi-phosphetan-2,4-dithion: Ein neues Reagens zur Schwefelung von N,N-disubstituierten Amiden".

Tetrahedron, vol. 40, No. 11, (month unavailable) 1984, pp. 2047-2052, B. Yde et al, "Studies on Organophosphorus Compounds XLVII[+] Preparation of Thiated Synthons of Amides, Lactams and Imides by Use of Some New P,S-Containing Reagents".

Tetrahedron, vol. 40, No. 14, (month unavailable) 1984, pp. 2663-2669, N.M. Yousif et al, Studies on Organophosphorus Compounds XLVIII.

Tetrahedron Letters, vol. 24, No. 36, (month unavailable) 1983, pp. 3815-3818, G. Lajoie et al, "Facile Regioselective Formation of Thiopeptide Linkages from Oligopeptides With New Thionation Reagents".

Orgn. Synth. 62 (month unavailable) 1984, pp. 158-163, I. Thomsen et al, "Thiation with 2,4-Bis(4-Methoxyphenyl)-1,3,2,4-Dithiadiphosphetane 2,4-Disulfide: N-Methylthiopyrrolidone".

Tetrahedron, vol. 41, No. 23, (month unavailable) 1985, pp. 5595-5606, O.E. Jensen et al, "Studies on Amino Acids and Peptides VIII.[a] Synthesis and Crystal Structure of Two Monothiated Analogues of Boc-Gly-S-Ala-Aib-OMe".

(Continued)

*Primary Examiner*—Johann Richter
*Assistant Examiner*—Andriae M Holt
(74) *Attorney, Agent, or Firm*—Richard E. L. Henderson

(57) ABSTRACT

The present application relates to novel heterocyclic compounds, to processes for their preparation, and to their use as crop protection agents, particularly for controlling animal pests.

6 Claims, No Drawings

OTHER PUBLICATIONS

Liebigs Ann. Chem. (month unavailable) 1992, pp. 1081-1086, Roland Köster et al, "Sulfidierung ausgewählter Carbonsäure- und Kohlensäureamide mit dem (9-BBN)$_2$S-Reagenz[1a]".

Sulfur Reagents in Organic Synthesis, (month unavailable) 1944, Patrick Metzner et al, pp. 44-45,"Thioamides".

Justus Liebigs Ann. Chem., vol. 641, pp. 1-39, (month unavailable) 1961, Hans Meerwein et al, "Über Säureamidacetale,Harnstoffacetale und Lactamacetale".

Tetrahedron Lett., 36(45), (month unavailable) 1995, pp. 8311-8314, Palanichamy Ilankumaran et al, "A Facile Conversion of Amides and Lactams to Thioamides and Thiolactams using Tetrathiomolybdate".

Tetrahedron, vol. 37, No. 21, (month unavailable) 1981, pp. 3635-3639, K. Clausen et al, "Studies on Amino Acids and Peptides-I".

Can. J. Chem., vol. 63, (month unavailable) 1985, pp. 3089-3101, Gilles Sauvé and Vanga S. Rao,"Backbone-modified oligopeptidic bioregulators. The synthesis and configuration of thioamide, amidoxime, cyanoamidine, and amidrazone analogs of the chemotactic peptide N-formyl-methionyl-leucyl-phenylalanine (f-Met-Leu-Phe-OR)".

J. Med. Chem. 31, (month unavailable) 1988, pp. 264-268, Mark G. Bock et al, "Cholecystokinin Antagonists. Synthesis and Biological Evaluation of 3-Substituted 1,4-Benzodiazepin-2-amines".

Aust J. Chem., 40, (month unavailable) 1987, pp. 491-499, Noel. W. Jacobsen et al, "Heterocyclic Variants of the Purine System. I Derivatives of Thiazolo[5,4-e]-1,2,4-triazine".

Radiobiologiya 22(2), (month unavailable) 1982, pp. 252-255, E.N. Goncharenko et al,"Role of Endogenous Substances in Enhancing Radioresistance Background".

Tetrahedron Lett., vol. 38, No. 52, (month available) 1997, pp. 8935-8938, Thomas Lindel and Holger Hoffmann, "Synthesis of Dispacamide from the Marine Sponge *Agelas dispar*".

Houben-Weyl, Methoden der Organischen Chemie, [Methods of Organic Chemistry], vol. XI/2 (month unavailable) 1958, pp. 99-117, H. Söll, "Umwandlung von primären und sekundären Aminen".

Soc. 97, (month unavailable) 1910, pp. 2099-2102, Frederick Daniel Chattaway, "A Simple Method of preparing Tetranitromethane".

J. Heterocycl. Chem., 7, Oct. 1970, pp. 1045-1049, W.J. Middleton et al, "Fluorinated Aminooxazolines. Synthesis and Properties".

Org. Synth. 59, (month unavailable) 1980, pp. 132-140, Geoffrey C. Crockett et al, "Photo-Chemical Ring Contraction of 2-Ethoxypyrrolin-5-Ones to Cyclopropanone Derivatives: *tert*-Butyl N-(1-Ethoxycyclopropyl)Carbamate".

Aust. J. Chem., 38, (month unavailable) 1985, pp. 1847-1856, Grant W. Heinicke et al, "Central Nervous System Active Compounds. XVI Some Chemistry of 6-Oxo Caprolactams Derived from an Enamine Ring-Expansion Synthesis".

Bull. Soc. Chim. Fr., 133, (month unavailable) 1996, pp. 625-635, Aïcha Amougay et al, "Réactions de photocycloaddition [2+2] intramoléculaire de N-alcénoyl-β-énaminones".

Synthesis, 20, (month unavailable) 1991, p. 176, Bharat B. Kikani et al, "An Efficient Synthesis Of 3-Aminocyclopent-2-en-1-one".

Tetrahedron Lett., 30(29), (month unavailable) 1989, pp. 3865-3868, Donald S. Middleton et al, "Synthesis of N-Protected Spiroamines Related to Natural Products Using Radical Cyclisations".

Can. J. Chem., 67(2), (month unavailable) 1989, pp. 213-219, Daniel Gardette et al, "Photo-cyclization of aryl enaminones. An efficient route to indole alkaloid synthons".

J. Heterocyclic Chem., 25, Nov.-Dec. 1988, pp. 1849-1856, Salma M. Abdelaal et al, Synthesis of 2-Amino-4-imino-4,5-dihydrothiazoles from N-Sulfonyl-α-chloroamidines and Thiourea [1].

Comprehensive Heterocyclic Chemistry, vol. 3, editors Alan R. Katritzky, and Charles W. Rees, (month unavailable) 1984, p. 96, D.J. Brown, "Pyrimidines and their Benzo Derivatives".

Chem. Pharm. Bull., 22(12), (month unavailable) 1974, pp. 2999-3001, Katsuhide Matoba et al "Reduction of O-Alkylated Imides".

Tetrahedron, vol. 41, No. 22 (month unavailable) 1985, pp. 5061-5087, Michael P. Cava et al, "Thionation Reactions of Lawesson's Reagents".

J. Org. Chem., 59, (month unavailable) 1994, pp. 348-354, D.C. Smith et al, Conversion of Amides and Lactams to Thioamides and Thiolactams Using Hexamethyldisilathiane.

Arch. Pharm. 32, (month unavailable) 1988, pp. 439-440, Hans-Dietrich Stachel et al, "Regioselektive α- und λ-Alkylierung von Thiotetronsäuren".

Aust. J. Chem., 32, (month unavailable), 1979, pp. 2025-2033, David St.C. Black et al, "Nitrones and Oxaziridines. XXVI Reaction of Grignard Reagents with 3-Oxo-1-pyrroline 1-Oxides and Synthesis of 2H-Pyrrole 1-Oxides".

J. Chem. Soc. (C), (month unavailable) 1971, pp. 257-259, G.P. Blackbourn et al, "Studies of the Reactions of Anhydrosulphites of α-Hydroxycarboxylic Acids. Part VI. Anhydrosulphite Synthesis and Characterisation".

Tetrahedron, vol. 41, No. 13 (month unavailable) 1985, pp. 2567-2624, R.A. Cherkasov et al, "Organothiophosphorus Reagents in Organic Synthesis".

Arch. Pharm., 303(8), Aug. 1970, pp. 625-633, K. Hartke et al, "N-Cyan-thiolimidoester und N,N'-Diccyan-amidine".

J. Chem. Soc. (C), (month unavailable) 1971, pp. 250-256, D.J. Brown, et al, "The Dimroth Rearrangement. Part XIII. The Small Effect of p-Substitution on Rearrangement Rates for 1,2-Dihydro-2-imino-1-methyl-5-phenylpyrimidines".

Aust. J. Chem., 35(10), (month unavailable) 1982, pp. 2025-2034, Leslie W. Deady et al, "Substituent Effects on the Isomer Ratios in the Rearrangement of Some 2- and 4-Nitraminopyridines".

Chem. Ind., 37, (month unavailable) 1985, pp. 730-732, Harry R. Ungerer, "Schiffsfarben—eine Spezialität der seenahen Lackindustrie".

AZOLES HAVING AN INSECTICIDAL ACTION

The present invention relates to novel heterocyclic compounds, to processes for their preparation and to their use as crop protection agents, in particular for controlling animal pests.

Various amino-substituted iminoheterocycles, such as, for example, 2-imino-4-amino-thiazoline, are already known as intermediates for dyes and active compounds or else as substances having a radio-protective effect. However, a use as crop protection agents and in particular for controlling animal pests has hitherto not been disclosed (cf. DE-A 2 921 683; S. M. Abdelall et al. J. heterocyclic Chem. 25, 1849-1956, 1988; E. N. Goncharenko et al. Radiobiologiya 22(2), 252-255, 1982).

Other amino-substituted iminoheterocycles, such as, for example, 3-amino- and 3-alkylamino-5-imino-2,5-dihydrofurans are known (cf. S. R. Landor J. Chem. Eoc. Perkin Trans. 1201-1204, 1991; M. Yu. Skvortsov et al. Zh. Org. Khim. 27(3), 526-530, 1991; M. Yu. Skvortsov et al. Zh. Org. Khim. 22(2), 255-259, 1986; M. Yu. Skvortsov et al., Zh. Org. Khim. 21(1), 221-222, 1985). Certain iminoheterocycles of this structural type, for example 2-imino-4-(2-hydroxyethylamino)-5,5-dimethyl-2,5-dihydrofuran, have anti-inflammatory and analgesic activity (cf. B. A. Trofimov et al. SU 1392872, 1998). However, nothing has been disclosed concerning the use as crop protection agents, in particular for controlling animal pests.

This invention now provides novel heterocyclic compounds of the formula (I)

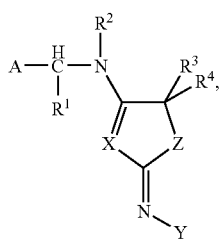

in which
A represents in each case optionally substituted aryl or hetaryl or heterocyclyl,
$R^1$ represents hydrogen or $C_1$-$C_3$-alkyl,
$R^2$ represents hydrogen or $C_1$-$C_3$-alkyl,
$R^3$ represents hydrogen or $C_1$-$C_3$-alkyl,
$R^4$ represents hydrogen or $C_1$-$C_3$-alkyl,
X represents N or CH,
Y represents CN or $NO_2$,
Z represents $CH_2$, O, S, SO, $SO_2$ or $NR^5$ and
$R^5$ represents hydrogen or $C_1$-$C_3$-alkyl.

Furthermore, it has been found that the compounds of the formula (I) are obtained when compounds of the formula (II)

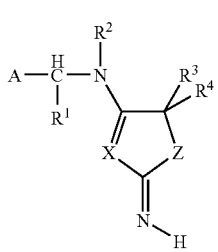

are reacted with suitable cyanating agents (to obtain compounds of the formula (I) in which Y represents CN) or with suitable nitrating agents (to obtain compounds of the formula (I) in which Y represents $NO_2$).

Finally, it has been found that the novel compounds of the formula (I) have strongly pronounced biological properties and are suitable especially for controlling animal pests, in particular insects, arachnids and nematodes, encountered in agriculture, in forests, in the protection of stored products and materials and in the hygiene sector.

The formula (I) provides a general definition of the compounds according to the invention.

Preferred substituents or ranges of the radicals listed in the formulae mentioned above and below are illustrated below.

A preferably represents optionally halogen-, cyano-, nitro-, $C_1$-$C_4$-alkyl-, $C_1$-$C_4$-haloalkyl-, $C_1$-$C_4$-alkoxy- or $C_1$-$C_4$-haloalkoxy-substituted phenyl.

A preferably further represents pyrazolyl, 1,2,4-triazolyl, oxazolyl, isoxazolyl, thiazolyl, isothiazolyl, 1,2,5-thiadiazolyl, pyridyl, pyrazinyl or pyrimidinyl, which are optionally substituted by fluorine, chlorine, bromine, cyano, nitro, $C_1$-$C_2$-alkyl (which is optionally substituted by fluorine and/or chlorine), $C_1$-$C_2$-alkoxy (which is optionally substituted by fluorine and/or chlorine), $C_1$-$C_2$-alkylthio (which is optionally substituted by fluorine and/or chlorine) or $C_1$-$C_2$-alkylsulfonyl (which is optionally substituted by fluorine and/or chlorine).

A furthermore preferably represents an optionally halogen- or $C_1$-$C_3$-alkyl-substituted saturated $C_5$-$C_6$-cycloalkyl radical in which one methylene group is replaced by O or S.

$R^1$ preferably represents hydrogen, methyl, ethyl, n-propyl or i-propyl.

$R^2$ preferably represents hydrogen, methyl, ethyl, n-propyl or i-propyl.

$R^3$ preferably represents hydrogen, methyl, ethyl, n-propyl or i-propyl.

$R^4$ preferably represents hydrogen, methyl, ethyl, n-propyl or i-propyl.

X preferably represents N or CH.

Y preferably represents CN or $NO_2$.

Z preferably represents $CH_2$, O, S or $NR^5$.

$R^5$ preferably represents hydrogen, methyl, ethyl, n-propyl or i-propyl.

A particularly preferably represents thiazolyl or pyridyl, which are each optionally substituted by halogen (in particular chlorine) or $C_1$-$C_3$-alkyl (in particular methyl).

A furthermore particularly preferably represents an optionally halogen- (in particular chlorine-) or $C_1$-$C_3$-alkyl- (in particular methyl-) substituted tetrahydrofuryl radical.

$R^1$ particularly preferably represents hydrogen or methyl.

$R^2$ particularly preferably represents hydrogen or methyl or ethyl.

$R^3$ particularly preferably represents hydrogen or methyl.

$R^4$ particularly preferably represents hydrogen or methyl.

X particularly preferably represents N or CH.

Y particularly preferably represents CN or $NO_2$.

Z particularly preferably represents $CH_2$, O, S or $NR^5$.

$R^5$ particularly preferably represents hydrogen or methyl.

A particularly preferably very particularly preferably represents one of the radicals

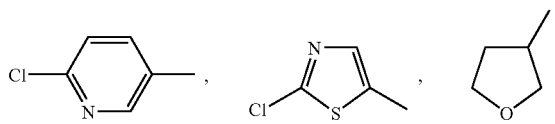

R[1] very particularly preferably represents hydrogen or methyl.
R[2] very particularly preferably represents methyl or ethyl.
R[3] very particularly preferably represents hydrogen or methyl.
R[4] very particularly preferably represents hydrogen or methyl.
X very particularly preferably represents N or CH.
Y very particularly preferably represents CN or NO$_2$.
Z very particularly preferably represents CH$_2$, O, S or NR[5].
R[5] very particularly preferably represents hydrogen or methyl.

In a particular group of compounds of the formula (I), X represents N.

In a further particular group of compounds of the formula (I), X represents CH.

In a further particular group of compounds of the formula (I), Y represents CN.

In a further particular group of compounds of the formula (I), Y represents NO$_2$.

In a further particular group of compounds of the formula (I), A represents

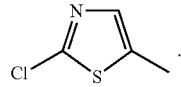

In a further particular group of compounds of formula (I), A represents

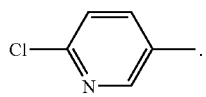

In a further particular group of compounds of the formula (I), A represents

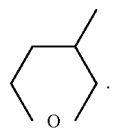

The general or preferred radical definitions or illustrations listed above apply to the end products and, correspondingly, to the starting materials and intermediates. The radical definitions can be combined with one another as desired, i.e. including combinations between the respective preferred ranges.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

In the radical definitions given above and below, hydrocarbon radicals, such as alkyl, are in each case straight-chain or branched as far as this is possible—including in combination with heteroatoms, such as in alkoxy.

Using, for example, the starting materials 4-(N-(6-chloro-3-pyridylmethyl)-N-methyl)amino-2-imino-2,5-dihydro-[1,3]-thiazoline and cyanogen bromide, the course of the process according to the invention can be represented by the reaction scheme below:

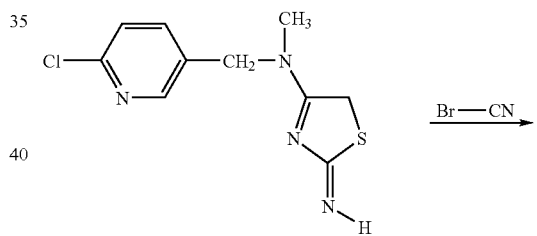

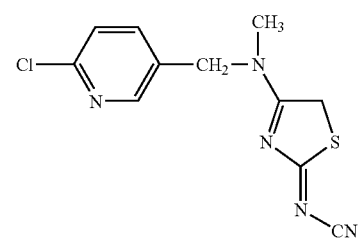

The compounds of the formula (II) are novel and also form part of the subject-matter of the present invention.

Depending in particular on the meaning of the variables X and Z, various methods may be considered for preparing the compounds of the formula (II). Some compounds of the formula (I), too, can be prepared by other methods.

This is illustrated initially by formula scheme I below.

Formula Scheme 1

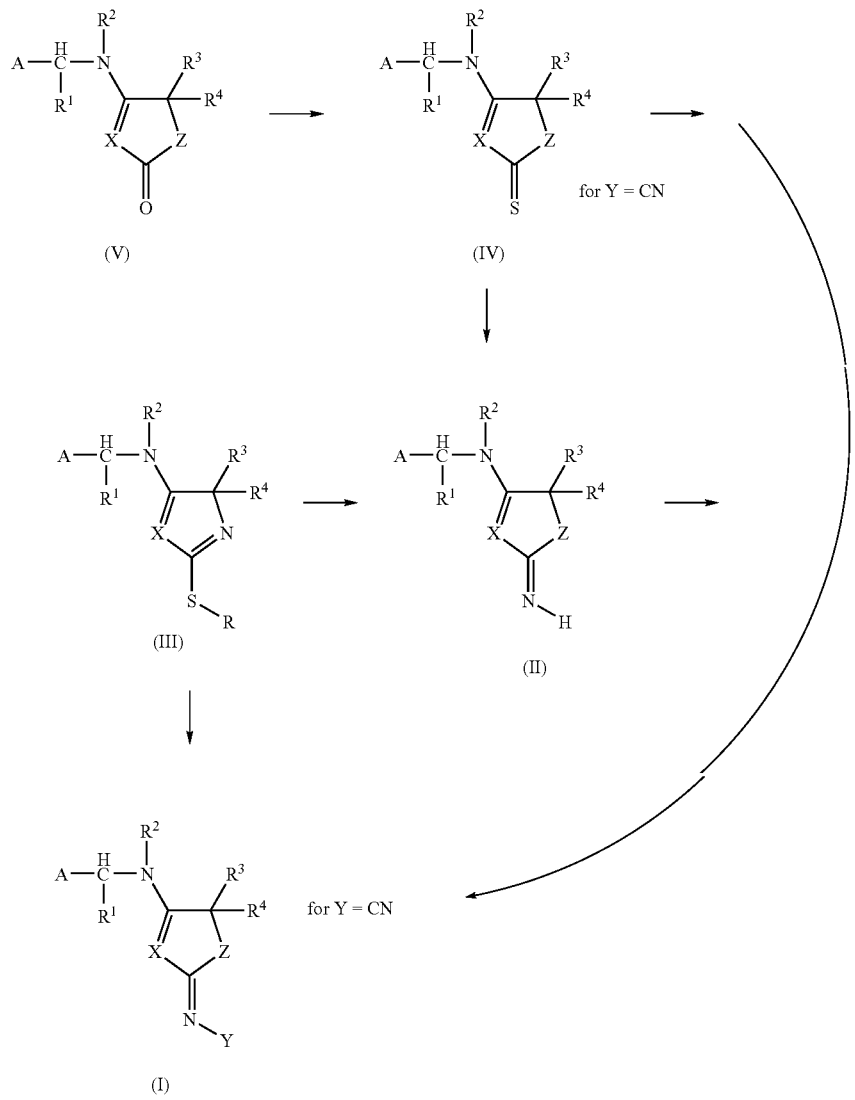

The reactions described in Formula Scheme I can be carried out in a generally known manner.

The compounds of the formula (V) can be converted by reaction with sulfurising reagents into the compounds of the formula (IV).

In the literature, a large number of different sulfurising agents, such as, for example, hydrogen sulfide ($H_2S$), hydrogen sulfide/hydrogen chloride ($H_2S/HCl$), hydrogen persulfide/hydrogen chloride ($H_2S_2/HCl$), di(diethylaluminium) sulfide [$(Et_2Al)_2S$], polymeric ethylaluminium sulfide [$(EtAlS)_n$], silicon disulfide ($SiS_2$), diboron trisulfide ($B_2S_3$), phosphorus pentachloride/dialuminium trisulfide/sodium sulfate ($PCl_5/Al_2S_3/Na_2SO_4$), sodium sulfide/sulfuric acid ($Na_2S/H_2SO_4$), diphosphorus pentasulfide ($P_2S_5$), diphosphorus pentasulfide/pyridine ($P_2S_5/Py$), diethylthiocarbamoyl chloride, diphosphorus pentasulfide/triethylamine ($P_2S_5/NEt_3$), diphosphorus pentasulfide/n-butyllithium ($P_2S_5/n$-BuLi), diphosphorus pentasulfide/sodium bicarbonate ($P_2S_5/NaHCO_3$; "Scheeren's Reagent", formation of $Na^{2+}$ [$P_4S_{10}O$]$^{2-}$), diphosphorus pentasulfide/methanol ($P_2S_5/$MeOH), SCN—CO—OEt, $PSCl_X (NMe_2)_{3-X}$ (X=0-3), bis (tricyclohexyltin)sulfide/boron trihalide [$(C_6H_{11})_3Sn]S_2^+ BX_3$ (X=Cl, F), EP 0280 867 (1988), bis(1,5-cyclooctanediylboryl) sulfide [$(9$-$BBN)_2S$] as sulfurising agent or as phosphorus pentasulfide substitute 2,4-bis(methylthio)-1,3,2,4-dithiadiphosphetane-2,4-disulfide "Davy Reagent Methyl" (DR-Me), 2,4-bis(ethylthio)-1,3,2,4-dithiadiphosphetane-2,4-disulfide "Davy Reagent Ethyl" (DR-Et), 2,4-bis(p-tolylthio)-1,3,2,4-dithiadiphosphetane 2,4-disulfide "Davy Reagent p-Tolyl or Heimgartner Reagent" (DR-T), 2,4-bis-(4-phenoxyphenyl)-2,4-dithioxo-1,3,2,4-dithiadiphosphetane "Belleau's Reagent (BR)", 2,4-bis-(4-phenylthiophenyl)-2,4-dithioxo-1,3,2,4-dithiadiphosphetane, 2,4-bis(4-methoxyphenyl)-2,4-dithioxo-1,3,2,4-dithiadiphosphetane "Lawesson's Reagent (LR)" (cf. Davy Reagent: H. Heimgartner et al., Helv. Chim. Acta 70, 1987, P. 1001; Belleau's Reagent: Tetrahedron 40, 1984, p. 2047; Tetrahedron 40, 1984, p. 2663; Tetrahedron Letters 24, 1983, p. 3815; I. Thomson et al., Org. Synth. 62, 1984, p. 158 and the literature cited therein; D. Brillon Synthetic Commun. 20

(19), 1990, P. 3085 and the literature cited therein; selective thionation of oligopeptides; K. Clausen et al., J. Chem. Soc., Perkin Trans I 1984, 785; O. E. Jensen et al., Tetrahedron 41, 1985, p. 5595; Reviews on "Lawesson's Reagent, (LR)": R. A. Cherkasov et al., Tetrahedron 41, 1985, p. 2567; M. P. Cava et al., Tetrahedron 41, 1985, p. 5061; diboryl sulfide: Liebigs Ann. Chem. 1992, p. 1081 and literature cited therein; Metzner et al. in Sulfur Reagents in Organic Synthesis, B. Harcourt: London 1994, Academic Press, p. 44-45) have been described in the literature.

Alternative possibilities are also reaction sequences such as, for example, O-alkylation with $R_3O^+BF_4^-$ (R: methyl, ethyl) (H. Meerwein et al., Justus Liebigs Ann. Chem. 641, (1961) p. 1) and subsequent reaction of the intermediates with anhydrous NaSH (R. E. Eibeck, Anorg. Syn. 7, (1963) p. 128), the in-situ formation of chloroiminium salts and subsequent reaction with tetrathiomolybdates, in particular benzyltriethylammonium tetrathiomolybdate $[(Ph-CH_2-NEt_3)_2 MoS_4]$ (Tetrahedron Lett. 36 (45), 1995, p. 8311) or hexamethyldisilathiane ($TMS_2S$) (TMS: trimethylsilyl; P. L. Fuchs et al., J. Org. Chem. 59, 1994, p. 348).

Preferred sulfurising agents are phosphorus reagents, such as, for example, diphosphorus pentasulfide ($P_2S_5$), diphosphorus pentasulfide/pyridine ($P_2S_5$/Py), diphosphorus pentasulfide/triethylamine ($P_2S_5$/NEt$_3$), diphosphorus pentasulfide/sodium bicarbonate ($P_2S_5$/NaHCO$_3$ "Scheeren's Reagent") or, particularly preferably, the racemisation-free 2,4-bis(4-methoxyphenyl)-2,4-dithioxo-1,3,2,4-dithiadiphosphetane (LR: Lawesson's Reagent) (K. Clausen, M. Thorsen, S.-O. Lawesson Tetrahedron 37, 1981, p. 3635), 2,4-bis-(4-phenoxyphenyl)-2,4-dithioxo-1,3,2,4-dithiadiphosphetane "Belleau's Reagent (BR)" or 2,4-bis-(4-phenylthiophenyl)-2,4-dithioxo-1,3,2,4-dithiadiphosphetane.

In general, it is advantageous to carry out this process in the presence of diluents. Diluents are advantageously employed in such an amount that during the entire process the reaction mixture remains readily stirrable. Suitable diluents for carrying out the process according to the invention are all inert organic solvents.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, anisole, phenetol, cyclohexyl methyl ether, dimethyl ether, diethyl ether, dipropyl ether, diisopropyl ether, di-n-butyl ether, diisobutyl ether, diisoamyl ether, ethyleneglycol dimethyl ether, tetrahydrofuran, dioxane, dichlorodiethyl ether and ethylene oxide and/or propylene oxide polyethers; amines, such as trimethylamine, triethylamine, tripropylamine, tributylamine, N-methyl-morpholine, pyridine and tetramethylenediamine; nitrated hydrocarbons such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example White Spirits having components of boiling points in the range of, for example, from 40° C. to 250° C., cymene, petroleum fractions within a boiling point range of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolinedione, N-formylpiperidine, N,N'-1, 4-diformylpiperazine; ketones, such as acetone, acetophenone, methyl ethyl ketone, methyl butyl ketone.

Process according to the invention can, of course, also be carried out in mixtures of the solvents and the diluents mentioned.

The diluents to be used depend on the sulfurising agent used in each particular case.

However, preferred diluents for the thionation are aromatic hydrocarbons, such as benzene, toluene, chlorobenzene, bromobenzene, nitrobenzene, or xylene, ethers, such as ethyl propyl ether, methyl tert-butyl ether, anisole, phenetol, cyclohexyl methyl ether, tetrahydrofuran or dioxane.

By reaction with $HgCl_2/(C_2H_5)_3N/H_2NCN$ the compounds of the formula (IV) can be converted directly into compounds of the formula (I) in which Y represents CN (cf. Can. J. Chem. 1985, 63, 3089 and also J. Med. Chem. 1988, 31, 264).

The compounds of the formula (IV) can furthermore be converted by aminolysis with ammonia in the presence of mercury salts, by heating in a reaction vessel with aqueous ammonia in the presence of suitable oxidizing agents, such as, for example, tert-butyl hydroperoxide (TBHP), into compounds of the formula (II) (cf. M. G. Bock et al., J. Med. Chem. 1988, 31, 264-268; N. W. Jacobsen et al., Aust. J. Chem. 1987, 40, 491-499; T. Lindel et al., Tetrahedron Lett. 1997. 38 (52), 8935-8938).

Reaction of the compounds of the formula (IV) (Z=NH) with alkyl iodides in the presence of bases gives compounds of the formula (III) (Z=N) (see T. Lindel et al., Tetrahedron Lett. 1997. 38, (52), 8935-8938; M. G. Bock et al., J. Med. Chem. 1988, 31, 264-268). In the compounds of the formula (III), R represents, for example, alkyl, preferably methyl. Compounds of the formula (III) in turn can be converted in a manner which is known in principle by reaction with a mixture of ammonia/ammonium chloride into compounds of the formula (II) (cf. T. Lindel et al., Tetrahedron Lett. 1997. 38, (52), 8935-8938).

The compounds of the formula (II) can be converted with cyanating agents or nitrating agents into compounds of the formula (I).

A suitable cyanating agent is, for example, cyanogen bromide (BrCN). The reaction is carried out in a generally known manner (cf. also U.S. Pat. No. 4,098,791 and DE 29 16 140).

Nitrations can be carried out by customary processes as described, for example, in Houben-Weyl, Methoden der Organischen Chemie, [Methods of Organic Chemistry], Volume XI/2 (Georg Thieme Verlag—Stuttgart 1958), pp. 99-116. Nitrating agents which may be mentioned are fumed or 100% strength nitric acid (preparation of anhydrous nitric acid cf. F. D. Chattaway, Soc. 97, 2100 (1910), if appropriate in the presence of sulfuric acid (W. J. Middleton et al., J. Heterocycl. Chem. 7, 1045-1049 (1970); L. W. Deady et al., Aust. J. Chem. 35 (10), 2025-2034 (1982); EP 0192060) or the use of nitric acid esters, acetyl nitrate or nitronium tetrafluoroborate. The reaction is preferably carried out in a generally known manner using acyl nitrate.

Compounds of the formula (Va)

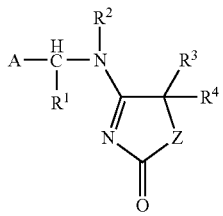

(Va)

in which
A, $R^1$, $R^2$, $R^3$ and $R^4$ are as defined above and
Z represents O or $CH_2$ are obtained, for example, by reacting amines of the formula (VI)

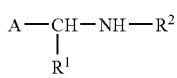

(VI)

in which
A, $R^1$ and $R^2$ are as defined above with compounds of the formula (VII)

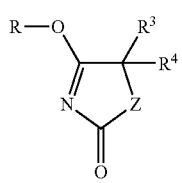

(VII)

in which
$R^3$, $R^4$ and Z are as defined above and
R represents hydrogen, methyl or ethyl, in the presence of a diluent, such as, for example, methanol or ethanol, at temperatures between 0° C. and 78° C.

Compounds of the formula (VII) and processes for their preparation are known, for example from Org. Synth. (1980), 59, 132 (for Z=$CH_2$).

Compounds of the formula (Vb)

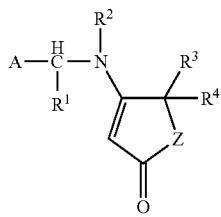

(Vb)

in which
A, $R^1$, $R^2$, $R^3$ and $R^4$ are as defined above and
Z represents $CH_2$, S or $NR^5$ and
$R^5$ is as defined above, are obtained, for example, by reacting amines of the formula (VI)

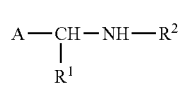

(VI)

in which
A, $R^1$ and $R^2$ are as defined above
with compounds of the formula (VIII)

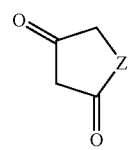

(VIII)

in which
Z represents $CH_2$, S or $NR^5$ and
$R^5$ is as defined above in the presence of a diluent, such as, for example, acetonitrile, ethanol, benzene, toluene, chlorobenzene, bromobenzene, nitrobenzene or xylene, and, if appropriate, in the presence of an acid catalyst, such as, for example, para-toluene sulfonic acid.

Preferred diluents are aromatic hydrocarbons, such as benzene, toluene or xylene.

The reaction is carried out at temperatures between −10° C. and +200° C., preferably between 0° C. and +150° C., particularly preferably at temperatures between +10° C. and +130° C. or at the boiling point of a suitable diluent. In principle, the reaction can be carried out under atmospheric pressure. The reaction is preferably carried out under atmospheric pressure and with removal of water, for example using a water separator or in the presence of molecular sieves.

The compounds of the formula (VIII) can also be present in the enol form. For compounds of the formula (VIII), cf., for example, Arch. Pharm. (Weinheim, Ger.), 321(7), 439, 1988; Aust. J. Chem. 38(12), 1847, 1985; Bull. Soc. Chim. Fr., 133(6), 625, 1996; Synthesis (2), 176, 1991; Tetrahedron Lett., 30(29), 3865, 1989; Can. J. Chem., 67(2), 213, 1989.

Compounds of the formula (IIIa)

(IIIa)

in which

A, $R^1$, $R^2$, $R^3$ and $R^4$ are as defined above and

R' represents alkyl, preferably methyl, are obtained, for example, by reacting compounds of the formula (IX)

(IX)

in which

A, $R^1$, $R^2$, $R^3$ and $R^4$ are as defined above initially in a diluent, such as, for example, an ether, with trimethylsilylisothiocyanate and then solubilising the intermediate formed, for example with methanol, and then reacting the intermediate of the formula (IIa) formed (IIa)

in which

A, $R^1$, $R^2$, $R^3$ and $R^4$ are as defined above initially with an alkyl halide, preferably an alkyl iodide, in particular methyl iodide, in the presence of a diluent, such as acetone, and then releasing the end product of the formula (IIIa) with a base, such as sodium carbonate, in the presence of a diluent, such as acetone.

The compounds of the formula (IX) are novel and also form part of the subject-matter of the present invention.

The compounds of the formula (IX) are obtained, for example, by the following scheme (cf. Preparation Examples)

1. (COCl)$_2$
2. DMF
3. DABCO

NaN$_3$

Compounds of the formula (IIb)

(IIb)

in which

A, $R^1$, $R^2$, $R^3$ and $R^4$ are as defined above, are furthermore obtained by reacting compounds of the formula (VI)

(VI)

A—CH—NH—R$^2$
|
R$^1$ in which

A, $R^1$ and $R^2$ are as defined above with compounds of the formula (XII)

(XII)

in which $R^3$ and $R^4$ are as defined above in the presence of a diluent, such as methylene chloride, methanol or acetonitrile (cf. J. Chem. Soc., Perkin Trans. 1(5), 1201, 1991; Zh. Org. Khim., 27(3), 526, 1991).

It is also possible to convert the compounds of the formula (III) directly into those compounds of the formula (I) in which Y represents CN. Suitable methods are described, for example, in JP 7126483 and Arch. Pharm., 303 (8), 625-633 (1970), the contents of which are expressly incorporated in this application by way of reference.

Compounds of the formula (Ia)

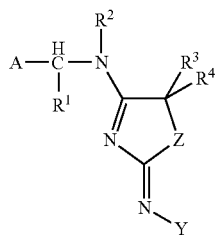

in which
A, $R^1$, $R^2$, $R^3$, $R^4$ and Y are as defined above and
Z represents S, are furthermore obtained, for example, by reacting compounds of the formula (X)

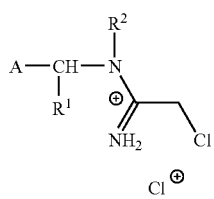

in which
A, $R^1$ and $R^2$ are as defined above, with potassium N-cyano(nitro)iminomethylsulphanyl-methanethiolate of the formula (XI)

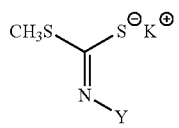

in which
Y is as defined above in the presence of a diluent.

Compounds of the formula (I) in which Z represents S can also be prepared according to J. Heterocyclic Chem. 25, 1849-1856 (1988), according to the reaction equation below:

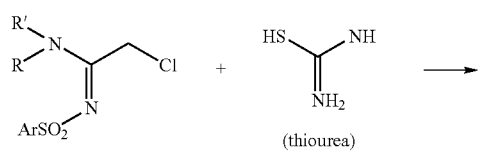

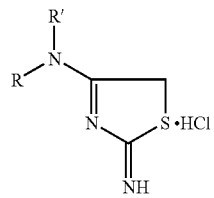

The compounds of the formula (X) are obtained, for example, by reacting compounds of the formula (VI)

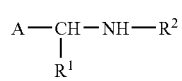

in which
A, $R^1$ and $R^2$ are as defined above, in the presence of a diluent, such as methanol, and in the presence of a base, such as sodium methoxide, with chloroacetonitrile.

The compounds of the formula (I) in which Z represents SO or $SO_2$ can be prepared from the compounds of the formula (I) in which Z represents S by oxidation according to customary processes, for example using suitable oxidising agents, such as peroxides, for example, hydrogen peroxide, tert-butyl peroxide, organic and inorganic peroxides or salts thereof, such as 3-chloroperbenzoic acid, peracetic acid, performic acid, dibenzoyl peroxide, permanganate, or using a mixture of potassium peroxomonosulphate, 2 $KHSO_5$, $KHSO_4$ and a solvent or solvent mixture (for example water, acetic acid, methanol, methylene chloride).

The peroxide can also be prepared in situ from another peroxide, for example peracetic acid from acetic acid and hydrogen peroxide (cf. also A. R. Katritzky, C. W. Rees in Comprehensive Heterocyclic Chemistry, Pergamon Press, Oxford, New York, 1984, Vol. 3, p. 96; D. J. Brown et al. Chem. Soc. (c), 1971, p. 256).

The oxidation can also be initiated or accelerated by suitable catalysts.

The active compounds having good plant tolerance and favourable warm-blood toxicity are suitable for controlling animal pests, in particular insects, arachnids and nematodes, which are encountered in agriculture, in forestry, in the protection of stored products and of materials, and in the hygiene sector. They may be preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp. and *Schistocerca gregaria*.

From the order of the Blattaria, for example, *Blatta orientalis*, *Periplaneta americana*, *Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp. and *Damalinia* spp.

From the order of the Thysanoptera, for example, *Hercinothrips femoralis*, *Thrips tabaci*, *Thrips palmi* and *Frankliniella accidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp. and *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp. and *Brevipalpus* spp.

The plant-parasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The compounds of the formula (I) according to the invention are active, in particular, against sucking insects.

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant cultivars protectable or not protectable by plant breeders' rights. Plant parts are to be understood to mean all above-ground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Solid Carriers are:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example ligno-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide, 4-methyl-tetrazolo[1,5-a]quinazolin-5(4H)-one,
8-(1,1-dimethylethyl)-N-ethyl-N-propyl-1,4-dioxaspiro[4.5]decane-2-methanamine, 8-hydroxyquinoline sulphate,
9H-xanthene-2-[(phenylamino)-carbonyl]-9-carboxylic hydrazide,
bis-(1-methylethyl)-3-methyl-4[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinatrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, Baculoviruses, *Beauveria bassiana, Beauveria tenella*, bendiocarb, benfuracarb, bensultap, benzoximate, betacyfluthrin, bifenazate, bifenthrin, bioethanomethrin, bio-permethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopren, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., eprinomectin, esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, metharhizium anisopliae, metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, selamectin, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetlyoxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

A mixture with other known active compounds, such as herbicides, or with fertilizers and growth regulators is also possible.

The active compounds according to the invention can furthermore be present when used as insecticides in their commercially available formulations and in the use forms, prepared from these formulations, as a mixture with synergistic agents.

Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp.,

*Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against *Aphis* spp. and *Myzus* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as being preferred—but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present context are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyes and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be protected.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with salt water or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using compounds according to the invention, alone or in combination with other active compounds, allows the use of heavy metals such as, for example, in bis-(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

Algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

Fungicides such as
benzo[b]thiophenecarboxylic acid cyclohexylamide S,S-dioxide, dichlofluanid, fluor-folpet, 3-iodo-2-propinyl butyl-carbamate, tolylfluanid and azoles such as azaconazole, cyproconazole, epoxyconazole, hexaconazole, metconazole, propiconazole and tebuconazole;

Molluscicides such as
fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulphone, 2-(N,N-di-methylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetra-methylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autunmalis, Dermatophagoides pteronissimus, Dermatophagoides forinae*.

From the order of the Araneae, for example, *Aviculariidae, Araneidae*.

From the order of the *Opiliones*, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example I-1

4-(N-(6-chloro-3-pyridylmethyl)-N-methyl)amino-2-cyanimino-2,5-dihydro-[1,3]-thiazoline

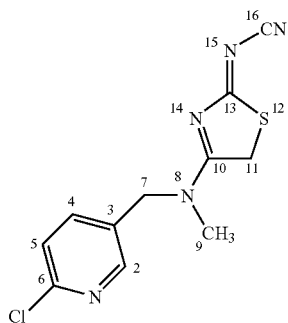

0.75 g (10.0 mmol) of chloroacetonitrile is added dropwise to a solution, cooled to 5° C., of 0.03 g (1.3 mmol) of sodium in 20 ml of abs. methanol. After the addition has ended, the mixture is stirred at this temperature for 1 hour, with exclusion of moisture. 1.93 g (10.0 mmol) of N,N-methyl-(6-chloro-3-pyridylmethyl)amine hydrochloride in 60 ml of abs. methanol are added dropwise over a period of 1 hour to this solution and the reaction mixture is warmed to room temperature and stirred for 20 hours. Under reduced pressure, the solvent is removed completely at room temperature using a rotary evaporator. The oily residue is, without further work-up, dissolved in 40 ml of acetone, 1.70 g (10.0 mmol) of potassium N-cyaniminomethyl-sulfanylmethanethiolate are added and the mixture is stirred at room temperature for five hours. The reaction mixture is concentrated using a rotary evaporator, resulting in the crystallisation of the product. The residue is filtered and recrystallised from ethanol.

Yield: 0.42 g (15% of theory) $C_{11}H_{10}ClN_5S$ (M=279.75 g/mol) MS (FAB/NBA matrix) m/z (%)=283 (5), 282 (31), 281 (15), 280 (80) [M+1]$^+$, 279 (7). IR (solid in KBr) $\nu$/cm$^{-1}$=2971 (C—H$_{alkyl}$), 2180 (C≡N), 1625 (C=N), 1588 and 1566 and 1458 (ring vibration), 1500 (C=N), 1407, 1381, 1300, 1264, 1221, 1097 ($C_{aryl}$—Cl), 879, 835.

Example I-2

4-(N-(2-chlorothiazol-5-yl)-N-ethyl)amino-2-cyanimino-2,5-dihydro-[1,3]-thiazoline

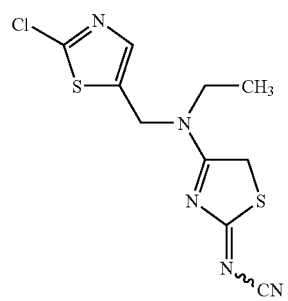

The cyclization is carried out analogously to the reaction procedure of Example I-1 using:

| | |
|---|---|
| 5.30 g (30 mmol) | N-ethyl-N-(2-chlorothiazol-5-yl-methyl)amine (cf. EP 302389 A2, 1989) |
| 2.26 g (30 mmol) | of chloroacetonitrile |
| 5.11 g (30 mmol) | of potassium N-cyaniminomethylsulfanylmethanethiolate |
| 0.10 g | of sodium |
| 240.9 ml | of methanol |
| 120.5 ml | of acetone |

The crude product thus remaining is prefractionated by reverse-phase (RP) chromatography using the mobile phase water (A)/methanol (B) (program—start: 50:50/step 1: 90% A, 10 min/step 2: 90% to 10% A, 90 min/step 3: 10% A, 10 min; pump lift about 40%). A second separation of the product obtained above (1.3 g) and subsequent preparative HPLC give pure 4-(N-(2-chlorothiazol-5-yl)-N-ethyl)amino-2-cyanimino-2,5-dihydro-[1,3]-thiazoline as an E/Z isomer mixture (cf. NMR).

$C_{10}H_{10}ClN_5S_2$ (M=299.8 g/mol) LC-MS (ESI positive) (m/z, %)=300 (MH$^+$, 100) R$_t$=3.54 min (0.1% HCOOH/acetonitrile) $^1$H-NMR (600 MHz, CD$_3$CN, TMS) δ=1.25 (3H, —CH$_3$); 3.50 (2H, —CH$_2$—); 4.48 (2H, —S—CH$_2$—); 4.90 (2H, —N—CH$_2$-Ct); 7.61 (1H, Ct-H) ppm. $^{13}$C— with $^1$H decoupling and $^1$H/$^{13}$C correlation (HMBC, HMQC, CD$_3$CN, TMS) δ=13.0 (—CH$_3$); 40.1 (—S—CH$_2$—); 40.8 (—S—CH$_2$—); 46.5 (—CH$_2$—); 46.6 (—CH$_2$—); 47.5 (—N—CH$_2$—); 117.9 (—CN); 135.6 (Ct-C); 142.5 (Ct-C); 153.5 (Ct-C—Cl); 178.7 (—N—C=N—); 181.4 (—N—C=N—); 191.0 (—C=N—); 191.9 (—C=N—) ppm. (E/Z isomer mixture). HPLC (water/acetonitrile)=3.17 min; $\lambda_{max}$=287.5 nm

Example I-3

5-Cyanimino-2-(N-(2-chlorothiazol-5-yl)-N-ethyl) aminopyrroline

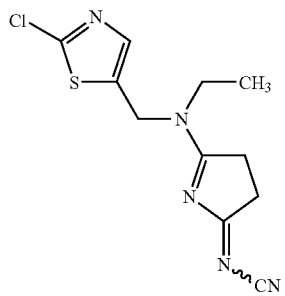

0.011 g (0.039 mmol) of 2-(N-(2-chlorothiazol-5-yl)-N-ethyl)aminopyrroline-5-thione (IV-1), 0.002 g (0.039 mmol) of cyanamide and 0.01 ml (0.039 mmol) of triethylamine are stirred in 5.0 ml of methanol, and under an atmosphere of protective gas (argon), 0.011 g (0.039 mmol) of mercury (II) chloride is added to the reaction mixture. After 15 minutes, the resulting suspension is filtered through silica gel 60—Merck (particle size: 0.04 to 0.063 mm) and the filtrate is concentrated under reduced pressure. The residue that remains is separated by reverse-phase (RP) chromatography using the mobile phase water (A)/methanol (B) (programme—Start: 50:50/step 1: 90% A, 10 min/step 2: 90% to 10% A, 90 min/step 3: 10% A, 10 min; pump lift about 40%). From the four fractions obtained, fractions two to four were repurified by RP chromatography using the mobile phase water (A)/methanol (B) (programme—Start: 50:50/Step 1: 90% A, 10 min/Step 2: 90% to 10% A, 90 min/Step 3: 10% A, 10 min; Pump lift about 40%).

Yield: 1.4 mg (0.05% of theory) $C_{11}H_{12}ClN_5S$ (M=281.7 g/mol) LC-MS (ESI positive) (m/z, %)=282 (MH⁺, 100) $R_t$=2.93 min (0.1% HCOOH/acetonitrile)

The compounds of the general formula (I) listed in Table I below can be prepared analogously to Examples I-1 to I-3.

isolation, the product is filtered, the solvent is removed under reduced pressure and the residue is chromatographed on silica gel using ethyl acetate/methanol 2/1. ($R_f$=0.2). The free base is obtained as a highly viscous oil.

Yield: 1.93 g (81% of theory) $C_{13}H_{17}ClN_4S$ (M=296.82 g/mol) MS (EI/70 eV) Zm/z (%)=298 (13), 297 (7), 296 (35), 283 (5), 281 (13), 226 (3), 224 (8), 170 (24), 128 (11), 126 (33), 115 (24), 100 (100), 99 (10), 89 (16), 82 (15), 74 (14), 58 (30), 56 (11), 43 (96). $^1$H-NMR$_{300}$ (DMSO-d$_6$/TMS) at 343 K δ/ppm=1.41 (s, 6 H, H-12 and -13), 2.36 (s, 3 H, H-18), 3.12

TABLE I

Examples of compounds of the formula (I)

(I)

| Ex. No. | A | $R^1$ | $R^2$ | $R^3$ | $R^4$ | X | Y | Z | Physical Data[a] |
|---|---|---|---|---|---|---|---|---|---|
| I-4 | Cl-pyridyl | —H | —Et | —H | —H | —N= | —CN | —S— | 294 (MH⁺, 100); 3.73 min |

[a] LC-MS (ESI positive) (m/z, %); $R_t$ (in min) (0.1% HCOOH/acetonitrile)

Example III-1

5-(N-(6-chloro-3-pyridylmethyl)-N-methylamino)-4,4-dimethyl-2-methylsulphanyl-4H-imidazole

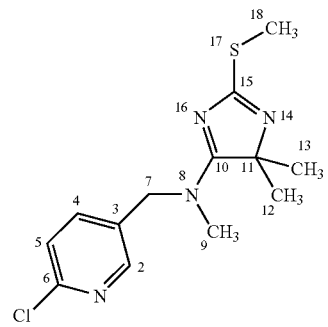

2.26 g (8.0 mmol) of 4-(N-(6-chloro-3-pyridylmethyl)-N-methyl)amino)-5,5-dimethyl-2,5-dihydro-1H-imidazole-2-thione are dissolved in 80 ml of abs. acetone, 3.40 g (24.0 mmol) of iodomethane in 10 ml of abs. acetone are added and the mixture is stirred at room temperature for four hours until all of the thione has reacted (monitored by TLC). Excess iodomethane and solvent are removed on a rotary evaporator under reduced pressure. To release the base, the oil that remains is taken up in 60 ml of acetone and stirred over solid sodium carbonate at room temperature for 14 hours. For (s, 3 H, H-9), 4.73 (s, 2 H, H-7), 7.48 (d, 1 H, H-5, J=8.2 Hz), 7.72 (dd, 1 H, H-4, J=8.2 Hz, J=2.5 Hz), 8.32 (d, 1 H, H-2, J=2.5 Hz).

Example IV-1

2-(N-(2-chlorothiazol-5-yl)-N-ethyl)aminopyrroline-5-thione

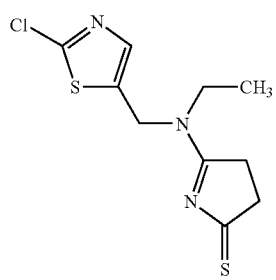

0.5 g (1.94 mmol) of 2-(N-(2-chlorothiazol-5-yl)-N-ethyl) aminopyrrolin-5-one (V-7) is stirred in 50 ml of tetrahydrofuran with 0.81 g (2,00 mmol) of 4-methoxyphenyldithiophosphonic acid anhydride (Lawesson's Reagent) at room temperature for 18 hours. The entire mixture is then filtered through a silica gel column (silica gel 60—Merck, particle size 0.04 to 0.063 mm) and the residue is washed with a mixture of ethyl acetate/methanol. The organic phase is concentrated under reduced pressure and the residue that remains is separated by reverse-phase (RP) chromatography using the mobile phase water (A)/methanol (B) (programme—Start: 50:50/Step 1: 90% A, 10 min/Step 2: 90% bis 10% A, 90 min/Step 3: 10% A, 10 min; pump lift about 40%). From the four fractions obtained, fractions two to four were repurified by RP chromatography using the mobile phase water (A)/methanol (B) (programme—Start: 50:50/Step 1: 90% A, 10 min/Step 2: 90% to 10% A, 90 min/Step 3: 10% A, 10 min; pump lift about 40%).

Yield: 0.01 g (1.8% of theory) $C_{10}H_{12}ClN_3S_2$ (M=273.8 g/mol) LC-MS (ESI positive) (m/z, %)=274 (MH$^+$, 100) $R_t$=3,12 min (0.1% HCOOH/acetonitrile) $^1$H-NMR (400 MHz, CDCl$_3$, TMS) δ=1.33 (3H, —CH$_3$); 2.88 (2H, —CH$_2$—); 3.23 (2H, —CH$_2$—); 3.48 (2H, —N—CH$_2$—); 5.00 (2H, —N—CH$_2$-Ct); 7.52 (1H, Ct-H) ppm. $^{13}$C with $^1$H decoupling and $^1$H/$^{13}$C correlation (HMBC, HMQC, CDCl$_3$, TMS) δ=13.4 (—CH$_3$); 30.6 (—CH$_2$—); 44.9 (—CH$_2$—); 45.1 (—N—CH$_2$—); 45.5 (—N—CH$_2$-Ct); 134.0, (Ct-C); 140.9 (Ct-C); 154.2 (Ct-C—Cl); 185.1 (—N—C=N—); 230.8 (C=S) ppm.

The compounds of the general formula (IV) listed in Table II below can be prepared analogously to Example IV-1.

Example IV-6

4-(N-(6-chloro-3-pyridylmethyl)-N-methylamino)-5,5-dimethyl-2,5-dihydro-1H-imidazole-2-thione

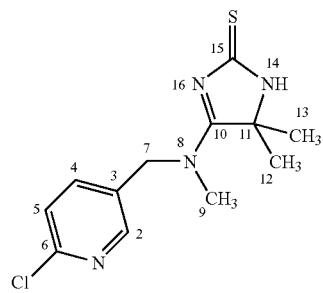

At room temperature, 1.31 g (10.0 mmol) of trimethylsilyl isothiocyanate in 10 ml of abs. diethyl ether are added dropwise under an atmosphere of nitrogen to 2.24 g (10.0 mmol)

TABLE II

Examples of compounds of the formula (IV)

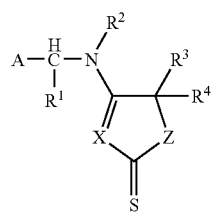

(IV)

| Ex. No. | A | R$^1$ | R$^2$ | R$^3$ | R$^4$ | X | Z | Physical Data$^{a)}$ |
|---|---|---|---|---|---|---|---|---|
| IV-2 | Cl-pyridyl | —H | —Me | —H | —H | —N= | —CH$_2$— | 254 (MH$^+$, 100); 2.49 min |
| IV-3 | Cl-pyridyl | —H | —Et | —H | —H | —N= | —CH$_2$— | 268 (MH$^+$, 100); 2.73 min |
| IV-4 | Cl-pyridyl | —H | —Me | —H | —H | —CH= | —S— | 271 (MH$^+$, 100); 3.80 min |
| IV-5 | Cl-pyridyl | —H | —Et | —H | —H | —CH= | —S— | 285 (MH$^+$, 100); 4.19 min |

$^{a)}$LC-MS (ESI positive) (m/z, %); R$_t$ (in min) (0.1% HCOOH/acetonitrile)

of 6-chloro-3-(N-(2,2-dimethyl-2H-azirin-3-yl)-N-methyl)-aminomethylpyridine in 30 ml of abs. diethyl ether. After the addition has ended, the reaction mixture is stirred for 20 minutes and hydrolysed with 4 ml of abs. methanol in 8 ml of abs. diethyl ether. The resulting solid is filtered, stirred in methanol for 2 hours and filtered again.

Yield: 2.69 g (95% of theory) MS (EI/70 eV) m/z (%)=284 (34), 283 (18), 282 (93), 281 (12), 269 (8), 267 (20), 247 (14), 156 (18), 128 (23), 127 (14), 126 (55), 101 (9), 100 (29), 99 (100), 83 (10), 72 (11), 58 (17), 42 (74), 41 (25). $^1$H NMR$_{300}$ (DMSO-d$_6$/TMS) δ/ppm=1.59 (s, 6 H, H-12 and H-13), 1.65 (s, 4.8 H, H-12 and H-13)*, 3.18 (s, 2.4 H, H-9)*, 3.23 (s, 3 H, H-9), 4.85 (s, 2 H, H-7), 5.01 (s, 1.6 H, H-7)*, 7.58 (t, 3.8 H, H-5, J=8.8 Hz), 7.84 (dd, 1 H, H-4, J=7.8 Hz, J<1 Hz), 7.93 (dd, 0.8 H, H-4, J=8.1 Hz, J<1 Hz)*, 8.42 (d, 1 H, H-2, J<1 Hz), 8.47 (d, 0.8 H, H-2, J<1 Hz)*, 10.09 (br, 1 H, H-14), 10.70 (br, 0.8 H, H-14)*.

Example V-1

2-(N-(2-chloropyrid-5-yl)-N-methyl)aminopyrrolin-5-one

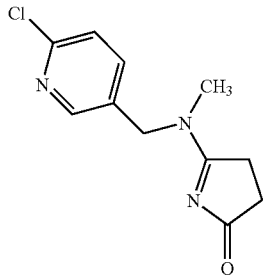

3.70 g (29.0 mmol) of 2-ethoxypyrrolin-5-one (cf. K. Matoba et al., *Chem. Pharm. Bull.* 1974, 22(12), 2999-3001; G. Crockett et al., *Org. Synth.* 1980, 59, 132-40) are dissolved in 60 ml of methanol, 4.4 g (29.0 mmol) of N-methyl-N-(2-chloropyrid-5-yl-methyl)amine (cf. EP 302389 A2, 1989) are added and the mixture is stirred at room temperature for 5 days. The entire reaction mixture is then concentrated under reduced pressure. The crystals that remain are stirred with 25 ml of ethanol and separated off.

Yield: 4.6 g (66.7% of theory) C$_{11}$H$_{12}$ClN$_3$O (M=237.7 g/mol) LC-MS (ESI positive) (m/z, %)=238 (MH$^+$, 100) R$_t$=1.08 min (0.1% HCOOH/acetonitrile) $^1$H-NMR (600 MHz, CDCl$_3$, TMS) δ=2.66 (2H, —CH$_2$—); 2.84 (2H, —CH$_2$—); 3.08 (3H, —N—CH$_3$); 4.88 (2H, —CH$_2$—Cl-Py); 7.31 (1H, Cl-Py-H); 7.78 (1H, Cl-Py-H); 8.34 (1H, Cl-Py-H) ppm. $^{13}$C with $^1$H decoupling and $^1$H/$^{13}$C correlation (600 MHz, HMBC, HMQC, CDCl$_3$, TMS) δ=28.4 (—CH$_2$—); 31.9 (—CH$_2$—); 35.5 (—N—CH$_3$); 51.4 (—N—CH$_2$—Cl-Py); 124.5 (Cl-Py-C), 139.3 (Cl-Py-C); 149.2 (Cl-Py-C); 151.2 (Cl-Py-C—Cl); 185.5 (—C=); 192.7 (C=O) ppm. HPLC (0.05M NH$_4$HCO$_3$/acetonitrile)= 1.41 min; λ$_{max}$=238 nm Example V-2

4-(N-(2-chlorothiazol-5-yl)-N-methyl)amino-2(5H)-thiophenone

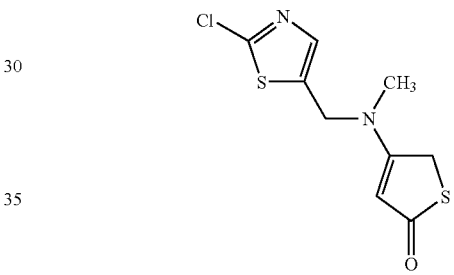

1.32 g (11.4 mmol) of 4-hydroxy-2(5H)-thiophenone (EP 189096 A1, 1986) and 1.85 g (11.4 mmol) of N-methyl-N-(2-chlorothiazol-5-yl-methyl)amine (cf. EP 302389 A2, 1989) in 57 ml of toluene are stirred in the presence of 17.1 g of molecular sieve 4 Å under protective gas (argon) at reflux temperature on a water separator for 12 hours. The entire reaction mixture is then concentrated under reduced pressure and the residue that remains is separated on a silica gel column (silica gel 60—Merck, particle size: 0.04 to 0.063 mm) using the mobile phase ethyl acetate.

Yield: 0.20 g (6.4% of theory) C$_9$H$_9$ClN$_2$OS$_2$ (M=260.7 g/mol) LC-MS (ESI positive) (m/z, %)=261 (MH+, 100) R$_t$=3.33 min (0.1% HCOOH/acetonitrile) $^1$H-NMR (400 MHz, CD$_3$CN, TMS) δ=2.99 (3H, —CH$_3$); 4.06 (2H, —CH$_2$—); 4.61 (2H, —N—CH$_2$-Ct); 5.15 (1H, —CH=); 7.50 (1H, Ct-H) ppm.

The compounds of the general formula (V) listed in Table III below can be prepared analogously to Examples V-1 and V-2.

TABLE III

Examples of compounds of the formula (V)

(V)

| Ex. No. | A | R¹ | R² | R³ | R⁴ | X | Z | Physical Data[a] |
|---|---|---|---|---|---|---|---|---|
| V-3 | 6-chloropyridin-3-yl | —H | —Me | —H | —H | —CH= | —S— | 255 (MH⁺, 100); 3.10 min |
| V-4 | 6-chloropyridin-3-yl | —H | —Et | —H | —H | —CH= | —S— | 269 (MH⁺, 100); 3.61 min |
| V-5 | 6-chloropyridin-3-yl | —H | —Et | —H | —H | —N= | —CH$_2$— | 252 (MH⁺, 100); 1.65 min |
| V-6 | 2-chlorothiazol-5-yl | —H | —Me | —H | —H | —N= | —CH$_2$— | 244 (MH⁺, 100); 1.39 min |
| V-7 | 2-chlorothiazol-5-yl | —H | —Et | —H | —H | —N= | —CH$_2$— | 258 (MH⁺, 100); 2.16 min |

[a] LC-MS (ESI positive) (m/z, %); R$_t$ (in min) (0.1% HCOOH/acetonitrile)

Example IX-1

6-chloro-3-(N-(2,2-dimethyl-2H-azirin-3-yl)-N-methyl)-aminomethylpyridine

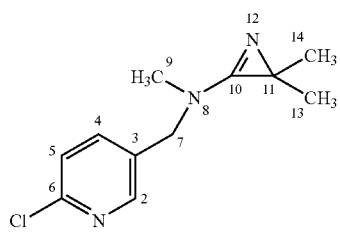

In a secured 250 ml four-necked flask fitted with dropping funnel, internal thermometer and dry-ice condenser on an ice-bath, 1.78 g (9.0 mmol) of diphosgene are initially charged in 20 ml of abs. CH$_2$Cl$_2$. At 0-5° C. and under nitrogen, a solution of 3.63 g (15.0 mmol) of N-(6-chloro-3-pyridylmethyl)-N-methyl-2-methylpropanethioamide in 10 ml of abs. CH$_2$Cl$_2$ are added dropwise. Four drops of abs. DMF are then added and the reaction mixture is slowly warmed to room temperature and stirred for four hours. Excess phosgene and solvent are then removed completely under water-pump vacuum via a cold trap. The solid that remains is, under nitrogen, dissolved in 60 ml of abs. THF and cooled to 0-5° C., and 1.68 g (15.0 mmol) of DABCO are added with vigorous stirring. The reaction mixture is warmed to room temperature and stirred for 45 minutes. The resulting voluminous precipitate is filtered under inert gas via an elbow fitting and washed twice with ab. THF. Under nitrogen, without further work-up, 1.95 g (30 mmol) of solid sodium azide are added to the resulting clear solution and the mixture is stirred for 48 hours. To isolate the product, the inorganic salts are filtered off, the solvent is removed under reduced pressure and the resulting residue is purified by silica gel column chromatography using the mobile phase ethyl acetate/methanol=10/2 (R$_f$=0.2).

Yield: 1.92 g (57% of theory) C$_{11}$H$_{14}$ClN$_3$ (M=223.71 g/mol) MS (EI/70 eV) m/z (%)=224 (6), 222 (13), 178 (17), 128 (3), 126 (10), 99 (5), 97 (100), 70 (11), 68 (14), 57 (10), 56 (17), 44 (10), 43 (16), 42 (15), 41 (19), 40 (19), 39 (7). $^1$H-NMR$_{300}$ (DMSO-d$_6$/TMS) at 373K δ/ppm=1.22 (s, 6 H, H-13 and H-14), 2.90 (s, 3 H, H-9), 4.44 (s, 2 H, H-7), 7.47 (dd, 1 H, H-5, J=8.2 Hz, J<1 Hz), 7.73 (ddt, 1 H, H-4, J=8.2 Hz, J=2.5 Hz, J<1 Hz), 8.33 (dd, 1 H, H-2, J=2.5 Hz, J<1 Hz).

Example

N-(6-chloro-3-pyridylmethyl)-N-methyl-2-methyl-propanethioamide

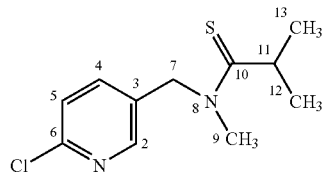

In a 250 ml two-necked flask, N-(6-chloro-3-pyridylmethyl)-N-methyl-2-methylpropanamide (6.80 g, 30.0 mmol) is dissolved in 120 ml of benzene, 1.47 g (3.3 mmol) of phosphorus pentasulfide are added and the mixture is heated at reflux for 1.5 hours. After this period of time, the mixture is cooled to room temperature and filtered, and the filtrate is concentrated under reduced pressure using a rotary evaporator. To increase the yield on the same day, the product should be subjected to silica gel column chromatography using the mobile phase dichloromethane/diethyl ether 10/3; $R_f$=0.8.

m.p.: 56°c. Yield: 5.16 g (71% of theory) $c_{11}H_{15}ClN_2S$ (M=242.77 g/mol) MS (EI/70 eV) m/z (%)=245 (5), 244 (38), 243 (16), 242 (100) [M+], 211 (15), 210 (6), 209 (51), 170 (7), 169 (4), 168 (10), 167 (8), 129 (6), 128 (23), 127 (18), 126 (67), 116 (32), 103 (8), 101 (5), 99 (13), 98 (28), 90 (13), 88 (16), 87 (56), 84 (22), 83 (39), 82 (13), 75 (12), 74 (16), 73 (13), 70 (22), 45 (14), 43 (14), 42 (44), 41 (13). $^1$H-NMR$_{300}$ (CDCl$_3$/TMS)*=two sets of signals owing to amide resonance δ/ppm=1.25 (d, 1.2 H, H-12 and H-13, $^3$J=6.5 Hz)*, 1.26 (d, 6 H, H-12 and H-13, $^3$J=6.5 Hz), 3.14 (sept, 0.2 H, H-11, $^3$J=6.5 Hz)*, 3.21 (sept, 1 H, H-11, $^3$J=6.5 Hz), 3.29 (s, 0.6 H, H-9), 3.47 (s, 3 H, H-9)*, 4.93 (s, 0.4 H, H-7)*, 5.37 (s, 2 H, H-7), 7.31 (d, 1 H, H-5, J=8.2 Hz), 7.36 (d, 0.2 H, H-5, J=8.2 Hz)*, 7.43 (dd, 0.2 H, H-4, J=8.2 Hz, J=2.5 Hz)*, 7.71 (dd, 1 H, H-4, J=8.2 Hz, J=2.5 Hz), 8.24 (d, 0.2 H, H-2, J=2.5 Hz)*, 8.32 (d, 1 H, H-2, J=2.4 Hz).

Potassium N-cyanoiminomethylsulphanylmethanethiolate (XI)

a) Preparation of the Dipotassium Salt of Cyanoimidodithiocarbonic Acid

Under an atmosphere of nitrogen, in a 500 ml four-necked flask fitted with overhead stirrer, dropping funnel, thermometer and reflux condenser, 21.0 g (0.50 mol) of cyanamide in 40 ml of ethanol are cooled to 0° C. At this temperature, 41.9 g (0.55 mol) of carbon disulfide and then 56.1 g (1.00 mol) of potassium hydroxide in 180 ml of ethanol are successively added dropwise such that the internal temperature does not exceed 5° C. (about 4 hours). After the addition has ended, the cooling bath is removed and the mixture is stirred at room temperature overnight. The resulting solid is filtered off, washed with ethanol and dried under reduced pressure. The resulting salt is hygroscopic and, during filtration, should only be in contact with the atmosphere/atmospheric humidity for a short time. For the next step, the salt is used as crude product. The yield is 75-80% of theory.

b) Potassium N-cyaniminomethylsulfanylmethanethiolate 77.7 g (0.40 mol) of the crude product are dissolved in a mixture of 270 ml of acetone and 300 ml of water and cooled to 0° C. At this temperature, with vigorous stirring, 56.8 g (0.40 mol) of methyliodide in 150 ml of acetone are slowly added dropwise over a period of three hours. After the addition has ended, the reaction mixture is stirred at 0° C. for one hour and then at room temperature for another three hours. On a rotary evaporator, all solvents are removed to dryness. The residue is taken up in 250 ml of abs. acetone and, using a rotary evaporator, concentrated to half of its original volume. For crystallisation of the resulting potassium iodide, the reaction mixture is kept in a fridge overnight. The resulting solid is filtered off and the filtrate is concentrated further, almost to dryness. In the cold, the desired product precipitates out. The last step can now be repeated to complete remove the potassium iodide. The yield is 75-80% of theory. The analytical data are consistent with the literature.

USE EXAMPLES

Example A

Meloidogyne Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita egg larvae suspension and lettuce seeds. The lettuce seeds germinate and the plants develop. On the roots, galls are formed.

After the desired period of time, the nematicidal action is determined in % using gall formation as a measure. 100% means that no galls were found; 0% means that the number of galls on the treated plants corresponds to that of the untreated control.

TABLE A

Plant-damaging nematodes
Meloidogyne Test

| Active compounds | Concentration of active compound in ppm | Kill rate in % after 14 days |
|---|---|---|
| Compound according to Example (I-1) | 20 | 98 |

Test with Cat Fleas/Oral Uptake

| | |
|---|---|
| Test animals: | Adults of *Ctenocephalides felis* |
| Solvent: | Dimethyl sulphoxide (DMSO) |

To produce a suitable preparation, a suitable solution of active compound is prepared from 20 mg of active compound and 1 ml of DMSO. 20 µl of this formulation are added to 4 ml of citrated cattle blood and stirred.

20 unfed adult fleas (*Ctenocephalides felis*, strain "Georgi") are placed into a chamber (Ø 5 cm) whose top and bottom are closed with gauze. A metal cylinder whose underside is covered with parafilm is placed onto the chamber. The cylinder contains the 4 ml of blood/active compound formulation which can be taken up by the fleas through the parafilm membrane. Whereas the blood is warmed to 37° C., the temperature in the area of the flea chambers is adjusted to 25° C. Controls are mixed with the same volume of DMSO, without addition of a compound. The determinations are carried out triplicate.

After 24 h, the mortality in % is determined.

Compounds which effect an at least 25% kill of the fleas within 24 h are judged to be effective.

In this test, for example, the following compounds of the Preparation Examples are effective:

| Compound | % action (mortality of larvae) 100 ppm |
|---|---|
| I-1 | 30 |

What is claimed is:

1. A compound of formula (I)

$$A-\underset{R^1}{\overset{H}{\underset{|}{C}}}-\underset{R^2}{\overset{|}{N}}\diagdown\underset{\underset{N\diagdown Y}{\overset{\|}{X}}}{\overset{R^3}{\underset{|}{C}}}R^4$$

(I)

in which
A represents substituted aryl or hetaryl or heterocyclyl,
$R^1$ represents hydrogen or $C_1$-$C_3$-alkyl,
$R^2$ represents hydrogen or $C_1$-$C_3$-alkyl,
$R^3$ represents hydrogen or $C_1$-$C_3$-alkyl,
$R^4$ represents hydrogen or $C_1$-$C_3$-alkyl,
X represents N or CH,
Y represents CN or $NO_2$,
Z represents $CH_2$, O, S, SO, $SO_2$, or $NR^5$, and
$R^5$ represents hydrogen or $C_1$-$C_3$-alkyl.

2. A compound of formula (I) according to claim 1 in which
A represents optionally halogen-, cyano-, nitro-, $C_1$-$C_4$-alkyl-, $C_1$-$C_4$-haloalkyl-, $C_1$-$C_4$-alkoxy-, or $C_1$-$C_4$-haloalkoxy-substituted phenyl; represents pyrazolyl, 1,2,4-triazolyl, oxazolyl, isoxazolyl, thiazolyl, isothiazolyl, 1,2,5-thiadiazolyl, pyridyl, pyrazinyl, or pyrimidinyl, each of which is optionally substituted by fluorine, chlorine, bromine, cyano, nitro, $C_1$-$C_2$-alkyl that is optionally substituted by fluorine and/or chlorine, $C_1$-$C_2$-alkoxy that is optionally substituted by fluorine and/or chlorine, $C_1$-$C_2$-alkylthio that is optionally substituted by fluorine and/or chlorine, or $C_1$-$C_2$-alkylsulfonyl that is optionally substituted by fluorine and/or chlorine; or represents an optionally halogen- or $C_1$-$C_3$-alkyl-substituted saturated $C_5$-$C_6$-cycloalkyl radical in which one methylene group is replaced by O or S,
$R^1$ represents hydrogen, methyl, ethyl, n-propyl, or i-propyl,
$R^2$ represents hydrogen, methyl, ethyl, n-propyl, or i-propyl,
$R^3$ represents hydrogen, methyl, ethyl, n-propyl, or i-propyl,
$R^4$ represents hydrogen, methyl, ethyl, n-propyl, or i-propyl,
X represents N or CH,
Y represents CN or $NO_2$,
Z represents $CH_2$, O, S, or $NR^5$, and
$R^5$ represents hydrogen, methyl, ethyl, n-propyl, or i-propyl.

3. A compound of formula (I) according to claim 1 in which
A represents thiazolyl or pyridyl, each of which is each optionally substituted by halogen or $C_1$-$C_3$-alkyl; or represents an optionally halogen- or $C_1$-$C_3$-alkyl-substituted tetrahydrofuryl radical,
$R^1$ represents hydrogen or methyl,
$R^2$ represents hydrogen or methyl or ethyl,
$R^3$ represents hydrogen or methyl,
$R^4$ represents hydrogen or methyl,
X represents N or CH,
Y represents CN or $NO_2$,
Z represents $CH_2$, O, S, or $NR^5$, and
$R^5$ represents hydrogen or methyl.

4. A compound of formula (I) according to claim 3 in which
A represents thiazolyl or pyridyl substituted by chlorine or methyl, or represents an optionally chlorine- or methyl-substituted tetrahydrofuryl radical.

5. A compound of formula (I) according to claim 1 in which
A represents one of the radicals $R^1$ represents hydrogen or methyl,
$R^2$ represents methyl or ethyl,
$R^3$ represents hydrogen or methyl,
$R^4$ represents hydrogen or methyl,
X represents N or CH,
Y represents CN or $NO_2$,
Z represents $CH_2$, O, S, or $NR^5$, and
$R^5$ represents hydrogen or methyl.

6. A method for controlling animal pests comprising applying a compound of formula (I) according to claim 1 to the animal pests and/or their habitat.

* * * * *